US005911133A

United States Patent [19]
Soble

[11] Patent Number: 5,911,133
[45] Date of Patent: Jun. 8, 1999

[54] USER INTERFACE FOR ECHOCARDIOGRAPHIC REPORT GENERATION

[75] Inventor: Jeffrey Scott Soble, Evanston, Ill.

[73] Assignee: Rush-Presbyterian -St. Luke's Medical Center, Chicago, Ill.

[21] Appl. No.: 08/956,135

[22] Filed: Oct. 22, 1997

[51] Int. Cl.$^6$ .............................. A61B 8/00; A61B 8/14; G06F 15/00; G06F 3/00
[52] U.S. Cl. ................................ 705/3; 600/450; 600/440
[58] Field of Search ........................... 705/2, 3; 600/450, 600/440

[56] References Cited

U.S. PATENT DOCUMENTS

| | | | |
|---|---|---|---|
| 3,864,660 | 2/1975 | Ranalli et al. | 367/11 |
| 3,909,792 | 9/1975 | Harris et al. | 600/519 |
| 5,090,413 | 2/1992 | Yoshika | 600/443 |
| 5,152,290 | 10/1992 | Freeland | 600/443 |
| 5,255,187 | 10/1993 | Sorensen | 364/413.02 |
| 5,262,943 | 11/1993 | Thibado et al. | 364/413.01 |
| 5,265,010 | 11/1993 | Evans-Paganelli et al. | 364/413.02 |
| 5,272,760 | 12/1993 | Echerer et al. | 382/6 |
| 5,322,066 | 6/1994 | Miyataka et al. | 600/440 |
| 5,384,862 | 1/1995 | Echerer et al. | 382/6 |
| 5,398,183 | 3/1995 | Elliott | 364/413.06 |
| 5,437,278 | 8/1995 | Wilk | 128/653.1 |
| 5,469,353 | 11/1995 | Pinsky et al. | 382/131 |
| 5,483,443 | 1/1996 | Milstein et al. | 364/401 |
| 5,513,101 | 4/1996 | Pinsky et al. | 705/3 |
| 5,549,117 | 8/1996 | Tacklind et al. | 128/716 |
| 5,586,262 | 12/1996 | Komatsu et al. | 705/2 |
| 5,617,313 | 4/1997 | Namiki | 705/3 |
| 5,655,084 | 8/1997 | Pinsky et al. | 475/140 |
| 5,660,179 | 8/1997 | Matsumoto et al. | 600/440 |
| 5,833,613 | 11/1998 | Averkiou et al. | 600/440 |

FOREIGN PATENT DOCUMENTS

| | | | |
|---|---|---|---|
| 8052140 | 2/1996 | Japan | A61B 8/14 |
| 2696997 | 9/1997 | Japan | G06T 5/00 |

OTHER PUBLICATIONS

Cochrane, T. and Dunlop, A.W., *A report generator package for routine laboratory tests in a hospital cardiology department*, Computer Methods and Programs in Biomedicine 20 (1985) 63–68.

Primary Examiner—Allen R. MacDonald
Assistant Examiner—James W. Myhre
Attorney, Agent, or Firm—Fitch, Even, Tabin & Flannery

[57] ABSTRACT

A computer-implemented user interface for generating an echocardiographic report includes a patient menu screen from which a user can select an existing report to modify or create a new report. After the user selects a patient, the first echocardiographic data screen, which includes a plurality of data entry windows for entering echocardiographic data, appears. At least one data entry window displays echocardiographic data for two paired cardiac structures and includes a button for selecting a desired one of the paired cardiac structures. The user selects whether data will be entered for one or the other of the paired cardiac structures, then inputs patient data through a series of buttons. Pairing of the cardiac structures saves on display real estate and takes advantage of commonality between the pairs. Paired cardiac structures include the left ventricle and right ventricle, the left atrium and right atrium, the aorta and pulmonary artery, mitral and tricuspid valve, and the aortic and pulmonary valve. Additionally, each data entry window includes means for displaying semi-quantitative echocardiographic data pertaining to a cardiac structure, from normal to markedly abnormal. Previous echocardiographic report data, if available, may be displayed for comparison with the current data. Upon completion of all data entries, an echocardiographic report is generated.

20 Claims, 28 Drawing Sheets

FIG. IA

Please use EXIT button on the bottom right to exit from ECHO REPORT

RUSH

Selection_

SELECT BY | READ STATUS: UNREAD

| | NAME | MR # | STUDY DATE | STUDY TYPE |
|---|---|---|---|---|
| 01 | HOUSTON, EDWARD | 9003943 | 9/12/1997 | DSE |
| 02 | BARAJAS, RAFAEL | 319290 | 9/12/1997 | TTE |
| 03 | HUGHES, DENNIS | 5165806 | 9/10/1997 | TTE |
| 04 | HUNT, DEAN | 393309 | 9/10/1997 | TTE |
| 05 | | | | |
| 06 | | | | |
| 07 | | | | |
| 08 | | | | |
| 09 | | | | |
| 10 | | | | |

TO FIG. IB

ACTION

READING | AMMEND | SEARCH | VIEW | NEW

FIG. 1B

| form 1 | | | | |
|---|---|---|---|---|

CardioNet

Please use EXIT button on the bottom right to exit from ECHO REPORT

| LOCATION | STUDY TYPE | | PAGE UP |
|---|---|---|---|
| ALL | ALL | | |

| READ STATUS | AMMEND | TAPE TYPE-YEAR-### | FOOTAGE | LOCATION | TECH |
|---|---|---|---|---|---|
| UNREAD | | SE-97-42 | 1:28:18-1:0:0 | IN_LAB | ? |
| UNREAD | | TTE-97-194 | 0:14:58-0:22:8 | ER_OBS | M. IN |
| UNREAD | | TXPLANT-97-2 | 0:0:0-0:7:30 | IN_LAB | M.CALLIS |
| UNREAD | | TXPLANT-97-1 | 1:44:0-1:54:15 | IN_LAB | M.CALLIS |

FROM FIG. 1A

| MODIFY | TSE-DSE MODIFY | SEND FAX | CHECK FAX | EXIT |
|---|---|---|---|---|

PAGE DOWN

FIG. 2A

CardioReportShell

VENTRICLES

○ LV  ○ RV

☐ Normal  ☐ NWV

Size
ED: 50   ES: 39   mm

L [ ][ ][ ][ ][ ][ ][ ][ ]
[ - ][ A ][ B ][ C ][ D ][ E ][ F ][ G ]
R [ ][ ][ ][ ][ ][ ][ ][ ]

Thickness
SEP [ ]   PW: [ ]   mm

L [ ][ ][ ][ ][ ][ ][ ][ ]
[ O ][ A ][ B ][ C ][ D ][ E ][ F ][ G ]
R [■][ ][ ][ ][ ][ ][ ][ ]

LVM: [ ] g/m  [ ] g/m

Function
%FS: [ ]   EF: [ ]

L [ ][ ][ ][ ][■][ ][ ][ ]
[ + ][ A ][ B ][ C ][ D ][ E ][ F ][ G ]
R [ ][■][ ][ ][ ][ ][ ][ ]

L <=== Wall Motion ===>R
☐ ☐ A   Normal            A ☐ ☐
☐ ☐ B   RWMA              B ☐ ☐
☐ ☐ C   No diag RWMA      C ☐ ☐
☐ ☐ D   Inadequate study  D ☐ ☐
☐ ☐ E   Diffuse Hypo Open   ▷

ATRIA

○ LA   ○ RA

☐ Normal   ☐ NWV

Size
AP: [ ]   IS: [ ]   mm

L [ ][ ][ ][ ][ ][ ][ ][ ]
[ - ][ A ][ B ][ C ][ D ][ E ][ F ][ G ]
R [ ][ ][ ][ ][ ][■][ ][ ]

Open   ▷

ARTERIES

○ AO   ○ PA

☐ Normal   ☐ NWV

Size
AO: [ ]   PA: [ ]   mm

A [ ][ ][ ][ ][ ][ ][ ][ ]
[ - ][ A ][ B ][ C ][ D ][ E ][ F ][ G ]
P [ ][ ][ ][ ][ ][ ][ ][ ]

Open   ▷

IVC
☐ ☐ A Normal
☐ [B] Abnormal
☐ ☐ C Not Well Visualized

CVP
[ O ][ A ][ B ][ C ][ D ][ E ][ F ][ G ]
[ ][ ][ ][ ][ ][ ][ ][ ]

TO FIG. 2B

[ Exit ] [ Generate ] [ Edit ] [ Sign ] [ Print/View ] [ Undo all ]

FIG. 2B

VALVES

○ Mitral     ○ Tricuspid
○ Aortic     ○ Pulmonic

☐ Normal     ☐ NWV

Regurgitation
| O | A | B | C | D | E | F | G |

M <=== Morphology ===> T
| ☐☐ | A | Normal | A ☐☐ |
| ☐☐ | B | Mild SCC/NST | B ☐☐ |
| ☐☐ | C | Mild MAC | C ☐☐ |
| ☐☐ | D | Abnormal | D ☐☐ |
| ☐☐ | E | Prosthesis | E ☐☐ |

M <=== Velocity ===> T
| ☐☐ | A | Normal | A ☐☐ |
| ☐☐ | B | Inc'd due to flow | B ☐☐ |
| ☐☐ | C | Decreased | C ☐☐ |
| ☐☐ | D | Stenotic | D ☐☐ |
| ☐☐ | E | Not obtained | E ☐☐ |

[ Open ]    [ ▷ ]

21. PA pressure
TR: [ 23 ]    [ ][ ] dm/s

| O | A | B | C | D | E | F | G |

OTHER

Pericardium/etc.
☐ ☐ A Normal
☐ ☐ B Minimal effusion
☐ ☑ C Abnormalities

Thrombus
☐ ☐ A None but LAA NWV
☐ ☐ B Inadequate to excl.
☐ ☐ C Thrombus

Miscellaneous
☐ ☐ A Congental
☐ ☑ B Contrast
☐ ☐ C No Vegetation
☐ ☐ D No Vegetation but CRO

Image quality
☐ ☐ A Technically difficult
☐ ☐ B Adequate
☐ ☑ C Good
☐ ☐ D Excellent
☐ ☐ E Limited

Comparison
☐ ☐ A Same as Previous
☐ ☐ B No signific. change
☐ ☑ C Significant change

[ Open ]    [ ◁ ]

HR: [ ]   BP: [ ] / [ ]
HT: [ ]   WT: [ ]   BSA: [ ]

FROM FIG. 2A stopFAX   C=6963 ROSENBLUM,LOUIS S311253 09/08/1997 TEE HR=1 BP138/8
        P=6831 ROSENBLUM,LOUIS S311253 09/02/1997 TTE HR=72 BP94/69

FIG. 3A

```
┌─────────────────────────────────────────────────────────┐
│ □                                        CardioReportShell │
│                                             VENTRICLES    │
│  ⦿ LV          ○ RV                                       │
│  ☐ Normal      ☐ NWV                                      │
│                                                            │
│  ┌─────── Size ────────┐  ┌──────── Diastolic ─────────┐ │
│  │ ED: 50   ES: 39  mm │  │        E/A ratio           │ │
│  │  L ▭▭▭▭▭▭▭          │  │  ☐ ☐ A  E/A normal         │ │
│  │    - A B C D E F G  │  │  ☐ ☐ B  E/A not obtained   │ │
│  │  R ▭▭▭▭▭▭▭          │  │  ☐ ☐ C  E/A fusion         │ │
│  └─────────────────────┘  │  ☐ ☐ D  NSR absent         │ │
│  ┌───── Thickness ─────┐  │  ☐ ☐ E  Fib/flutter        │ │
│  │ SEP       PW:    mm │  │  ☐ ☐ F  E/A < 1            │ │
│  │  L ▭▭▭▭▭▭▭          │  │  ☐ ☐ G  E/A >= 2           │ │
│  │    O A B C D E F G  │  └────────────────────────────┘ │
│  │  R ▭▭▭▭▭▭▭          │  ┌──── Deceleration Time ─────┐ │
│  └─────────────────────┘  │  ☐ ☐ A  Dt not obtained    │ │
│  LVM:      g/m     g/m    │  ☐ ☐ B  Dt > 230 msec      │ │
│  ┌───── Function ──────┐  │  ☐ ☐ C  Dt normal(150-230msec) │
│  │ %FS:      EF:       │  │  ☐ ☐ D  Dt 120-149 msec    │ │
│  │  L ▭▭▭▭▭▭▭          │  │  ☐ ☐ E  Dt < 120 msec      │ │
│  │    + A B C D E F G  │  └────────────────────────────┘ │
│  │  R ▭▭▭▭▭▭▭          │  ┌──── Pulmonary Vein Flow ───┐ │
│  └─────────────────────┘  │  ☐ ☐ A  S/D ratio normal   │ │
│  ┌ L <=== Wall Motion ===>R ┐│☐ ☐ B  S/D ratio not obtained│
│  │ ☐ ☐ A   Normal    A ☐ ☐│  │  ☐ ☐ C  S/D ratio < 0.5    │ │
│  │ ☐ ☐ B   RWMA      B ☐ ☐│  │  ☐ ☐ D  S/D ratio > 2.6 if >= 50 │
│  │ ☐ ☐ C   No diag RWMA C ☐ ☐│☐ ☐ E  S/D ratio > 1.5 if < 50 │
│  │ ☐ ☐ D   Inadequate study D ☐ ☐│ ☐ ☐ F  Pva velocity not obtained │
│  │ ☐ ☐ E   Diffuse Hypo │  │  ☐ ☐ G  Pva velocity  35 cm/s │
│  └────────────────────┘   │  ☐ ☐ H  Pva dur > Mva dur  │ │
│  ┌──────┐  ┌────┐         └────────────────────────────┘ │
│  │ Open │  │ ▷  │                                         │
│  └──────┘  └────┘                                         │
│                                                            │
│  ┌────┐ ┌────────┐ ┌────┐ ┌────┐ ┌──────────┐ ┌────────┐  │
│  │Exit│ │Generate│ │Edit│ │Sign│ │Print/View│ │Undo all│  │
│  └────┘ └────────┘ └────┘ └────┘ └──────────┘ └────────┘  │
└─────────────────────────────────────────────────────────┘
```

IVRT
- ☐ ☐ A  IVRT normal
- ☐ ☐ B  IVRT not obtained
- ☐ ☐ C  IVRT > 100 msec
- ☐ ☐ D  IVRT < = 60 msec
- ☐ ☐ E  IVRT respirophasic changes ☐ ☐  B-notch

Diastolic Function
- ☐ ☐ A  Normal
- ☐ ☐ B  Indeterminant
- ☐ ☐ C  -relax
- ☐ ☐ D  -relax / > =70
- ☐ ☐ E  -relax / dec. volume
- ☐ ☐ F  -relax / > =70 / dec. volume
- ☐ ☐ G  dec. volume
- ☐ ☐ H  -relax with +LVEDP
- ☐ ☐ I  Pseudonormal
- ☐ ☐ J  Restrictive

FROM FIG. 3A

Mass
- ☐ ☐ A  Cath/Pacing Lead
- ☐ ☐ B  Thrombus
- ☐ ☐ C  Undefined

Hypertrophy
- ☐ ☐ A  Concentric
- ☐ ☐ B  Eccentric
- ☐ ☐ C  ASH
- ☐ ☐ D  Apical
- ☐ ☐ E  HCM
- ☐ ☐ F  HOCM
- ☐ ☐ G  Focal basal septal

Interventricular Septum
- ☐ ☐ A  Diastolic Flat
- ☐ ☐ B  Systolic Flat
- ☐ ☐ C  Systolic + diastolic flat
- ☐ ☐ D  Paradoxic
- ☐ ☐ E  Dyssyner - RECEIVED
- ☐ ☐ F  Dyssyner - thoracotomy
- ☐ ☐ G  Dyssynergic NOS
- ☐ ☐ H  VSD

[ Close ]  [ ◁ ]

stop FAX  
C=6963 ROSENBLUM, LOUIS S311253 09/08/1997 TEE HR= 1 BP 138/8  
P=6831 ROSENBLUM, LOUIS S311253 09/02/1997 TTE HR= 72 BP 94/69

FIG. 4A

CardioReportShell

VENTRICLES

○ LV  ⦿ RV

☐ Normal  ☐ NWV

Size
ED: 50   ES: 39   mm

L [ | | | | | | | ]
[ − | A | B | C | D | E | F | G ]
R [ | | | | | | | ]

Thickness
SEP [  ]   PW: [  ]   mm

L [ | | | | | | | ]
[ O | A | B | C | D | E | F | G ]
R [ | | | | | | | ]

LVM: [  ] g/m  [  ] g/m

Function
%FS: [  ]   EF: [  ]

L [ | | | | | | | ]
[ + | A | B | C | D | E | F | G ]
R [ | | | | | | | ]

L <=== Wall Motion ===> R
☐☐ A   Normal           A ☐☐
☐☐ B   RWMA             B ☐☐
☐☐ C   No diag RWMA     C ☐☐
☐☐ D   Inadequate study D ☐☐
☐☐ E   Diffuse Hypo

Diastolic function
☐ ☐ A  Normal(E:A)
☐ ☐ B  B-notch
☐ ☐ C  inc. A vs E
☐ ☐ D  inc. E vs A
☐ ☐ E  Flat septum

Mass
☐ ☐ A  Cath/Pacing lead
☐ ☐ B  Thrombus
☐ ☐ C  Undefined

[ Open ]   [ ▷ ]

[ Exit ] [ Generate ] [ Edit ] [ Sign ] [ Print/View ] [ Undo all ]

CardioReportShell

| VENTRICLES | |
|---|---|
| ○ LV | ○ RV |
| ☐ Normal | ☐ NWV |

Size
ED: 50   ES: 39   mm

L [____]
[ - | A | B | C | D | E | F | G ]
R [████]

Thickness
SEP [__]   PW: [__]   mm

L [____]
[ O | A | B | C | D | E | F | G ]
R [████]

LVM: [__] g/m   [__] g/m

Function
%FS: [__]   EF: [__]

L [____]
[ + | A | B | C | D | E | F | G ]
R [████]

| L<=== Wall Motion ===>R | | |
|---|---|---|
| ☐☐ A | Normal | A ☐☐ |
| ☐☐ B | RWMA | B ☐☐ |
| ☐☐ C | No diag RWMA | C ☐☐ |
| ☐☐ D | Inadequate study | D ☐☐ |
| ☐☐ E | Diffuse Hypo | |

[ Open ]   [ ▷ ]

| | |
|---|---|
| ● LA | ○ RA |
| ☐ Normal | ☐ NWV |

Size
AP: [__]   IS: [__]   mm

L [____]
[ - | A | B | C | D | E | F | G ]
R [████]

LAA
☐ ☑ A  Normal
☐ ☐B  Dilated
☐ ☐  C  Reduced emptying
☐ ☐D  SEC
☐ ☑ E  No thrombus
☐ ☐  F  ?thrombus
☐ ☐  G  Thrombus

IVC
☐ ☐ A Normal
☐ ☐B Abnormal
☐ ☐ C Not Well Visualized

CVP
[ O | A | B | C | D | E | F | G ]

TO FIG. 5B

[ Exit ] [ Generate ] [ Edit ] [ Sign ] [ Print/View ] [ Undo all ]

FIG. 5B

| ATRIA | OTHER |

Septum
- ☐ ☐ A  Bowing L-to-R
- ☐ ☐ B  Bowing R-to-L
- ☐ ☐ C  Aneurysm
- ☐ ☐ D  Lip. hypertr.
- ☐ ☐ E  Thickened
- ☐ ☐ F  PFO
- ☐ [G] ASD
- ☐ ☐ H  NWV

Mass
- ☐ ☐ A  Myxoma
- ☐ ☐ B  Thrombus
- ☐ ☐ C  Prominent eustachian viv
- ☐ ☐ D  Chiari network
- ☐ ☐ E  Cath/Pacing lead
- ☐ ☐ F  Undefined

[ Close ]   [ ◁ ]
[ Open ]    [ ▷ ]

21. PA pressure
TR: [ 23 ]   [ | ] dm/s

| O | A | B | C | D | E | F | G |

FROM FIG. 5A

Pericardium/etc.
- ☐ ☐ A  Normal
- ☐ ☐ B  Minimal effusion
- ☐ ☑C  Abnormalities

Thrombus
- ☐ ☐ A  None but LAA NWV
- ☐ ☐ B  Inadequate to excl.
- ☐ ☐ C  Thrombus

Miscellaneous
- ☐ ☐ A  Congenital
- ☐ ☑B  Contrast
- ☐ ☐ C  No Vegetation
- ☐ ☐ D  No Vegetation but CRO

Image quality
- ☐ ☐ A  Technically difficult
- ☐ ☐ B  Adequate
- ☐ ☑ C  Good
- ☐ ☐ D  Excellent
- ☐ ☐ E  Limited

Comparison
- ☐ ☐ A  Same as Previous
- ☐ ☐ B  No signific. change
- ☐ ☑ C  Significant change

[ Open ]   [ ◁ ]

HR: [   ]   BP: [   ] / [   ]
HT: [   ]   WT: [   ]   BSA: [   ]

stopFAX
C=6963 ROSENBLUM,LOUIS S311253 09/08/1997 TEE HR=IBP138/8
P=6831 ROSENBLUM,LOUIS S311253 09/02/1997 TTE HR=72BP94/69

FIG. 6A

CardioReportShell

VENTRICLES

○ LV    ○ RV

☐ Normal    ☐ NWV

Size
ED: 50    ES: 39    mm

L [bar]
| - | A | B | C | D | E | F | G |
R [bar]

Thickness
SEP: ___    PW: ___    mm

L [bar]
| O | A | B | C | D | E | F | G |
R [bar]

LVM: ___ g/m    ___ g/m

Function
%FS: ___    EF: ___

L [bar]
| + | A | B | C | D | E | F | G |
R [bar]

L <=== Wall Motion ===> R

☐ ☐ A    Normal           A ☐ ☐
☐ ☐ B    RWMA             B ☐ ☐
☐ ☐ C    No diag RWMA     C ☐ ☐
☐ ☐ D    Inadequate study D ☐ ☐
☐ ☐ E    Diffuse Hypo

[ Open ]    [ ▷ ]

---

○ LA    ● RA

☐ Normal    ☐ NWV

Size
AP: ___    IS: ___    mm

L [bar]
| - | A | B | C | D | E | F | G |
R [bar]

LAA

☐ ☑ A Normal
☐ ☐ B Dilated
☐ ☐ C Reduced emptying
☐ ☐ D SEC
☐ ☑ E No thrombus
☐ ☐ F ?thrombus
☐ ☐ G Thrombus

IVC

☐ ☐ A Normal
☐ ☐ B Abnormal
☐ ☐ C Not Well Visualized

CVP
| O | A | B | C | D | E | F | G |

[ Exit ]  [ Generate ]  [ Edit ]  [ Sign ]  [ Print/View ]  [ Undo all ]

FIG. 7A

CardioReportShell

VENTRICLES

○ LV    ○ RV

☐ Normal    ☐ NWV

Size
ED: [50]    ES: [39]    mm

L [ ][ ][ ][ ][ ][ ][ ][ ]
[-][A][B][C][D][E][F][G]
R [ ][ ][ ][ ][ ][ ][ ][ ]

Thickness
SEP [ ]    PW: [ ]    mm

L [ ][ ][ ][ ][ ][ ][ ][ ]
[O][A][B][C][D][E][F][G]
R [ ][■][ ][ ][ ][ ][ ][ ]

LVM: [ ] g/m    [ ] g/m

Function
%FS: [ ]    EF: [ ]

L [ ][ ][ ][ ][■][ ][ ][ ]
[+][A][B][C][D][E][F][G]
R [ ][■][ ][ ][ ][ ][ ][ ]

L <=== Wall Motion ===> R
☐ ☐ A    Normal        A ☐ ☐
☐ ☐ B    RWMA          B ☐ ☐
☐ ☐ C    No diag RWMA  C ☐ ☐
☐ ☐ D    Inadequate study  D ☐ ☐
☐ ☐ E    Diffuse Hypo

[ Open ]    [ ▷ ]

ATRIA

○ LA    ○ RA

☐ Normal    ☐ NWV

Size
AP: [ ]    IS: [ ]    mm

L [ ][ ][ ][ ][ ][ ][ ][ ]
[-][A][B][C][D][E][F][G]
R [ ][ ][ ][ ][■][ ][ ][ ]

[ Open ]    [ ▷ ]

ARTERIES

● AO    ○ PA

☐ Normal    ☐ NWV

Size
AO: [ ]    PA: [ ]    mm

A [ ][ ][ ][ ][ ][ ][ ]
  [ ][ ][ ][ ][ ][ ][ ]
P [ ][ ][ ][ ][ ][ ][ ]

Dissection
☐ ☐ A None
☐ ☐ B Cannot K/O => TEE
☐ ☐ C Asc.
☐ ☐ D Arch
☐ ☐ E Desc.
☐ ☒ F Aneurysmal

TO FIG. 7B

[ Exit ] [ Generate ] [ Edit ] [ Sign ] [ Print/View ] [ Undo all ]

FIG. 8A

CardioReportShell

VENTRICLES

○ LV  ○ RV

☐ Normal  ☐ NWV

Size
ED: 50  ES: 39  mm

L
| - | A | B | C | D | E | F | G |
R

Thickness
SEP:  PW:  mm

L
| O | A | B | C | D | E | F | G |
R

LVM:  g/m  g/m

Function
%FS:  EF:

L
| + | A | B | C | D | E | F | G |
R

L <=== Wall Motion ===> R
☐ ☐ A  Normal      A ☐ ☐
☐ ☐ B  RWMA        B ☐ ☐
☐ ☐ C  No diag RWMA C ☐ ☐
☐ ☐ D  Inadequate study D ☐ ☐
☐ ☐ E  Diffuse Hypo Open  ▷

ATRIA

○ LA  ○ RA

☐ Normal  ☐ NWV

Size
AP:  IS:  mm

L
| - | A | B | C | D | E | F | G |
R

Open  ▷

ARTERIES

○ AO  ● PA

☐ Normal  ☑ NWV

Size
AO:  PA:  mm

A

P

Dissection
☐ ☐ A None
☐ ☐ B Cannot K/O => TEE
☐ ☐ C Asc.
☐ ☐ D Arch
☐ ☐ E Desc.
☐ ☐ F Aneurysmal

TO FIG. 8B

| Exit | Generate | Edit | Sign | Print/View | Undo all |

FIG. 8B

VALVES

○ Mitral   ○ Tricuspid
○ Aortic   ○ Pulmonic

☐ Normal   ☐ NWV

Regurgitation

| O | A | B | C | D | E | F | G |

M <=== Morphology ===> T

Aortic arch

☐ ☐ A  Normal
☐ ☐ B  Sessile < 4mm, mild
☐ ☐ C  Sessile < 4mm, moderate
☐ ☐ D  Sessile < 4mm, extensive
☐ ☐ E  Sessile >= 4mm, mild
☐ ☐ F  Sessile >= 4mm, moderate
☐ ☐ G  Sessile >= 4mm, extensive
☐ ☐ H  Pedunculated, mild
☐ ☐ I  Pedunculated, moderate
☐ ☐ J  Pedunculated, extensive
☐ ☐ K  Thrombus

[ Close ]  [ ◁ ]

OTHER

Pericardium/etc.
☐ ☐ A  Normal
☐ ☐ B  Minimal effusion
☐ ☑C  Abnormalities

Thrombus
☐ ☐ A  None but LAA NWV
☐ ☐ B  Inadequate to excl.
☐ ☐ C  Thrombus

Miscellaneous
] ☐ A  Congenital
] ☑B  Contrast
] ☐ C  No Vegetation
] ☐ D  No Vegetation but CRO

Image quality
] ☐ A  Technically difficult
] ☐ B  Adequate
] ☑C  Good
] ☐ D  Excellent
] ☐ E  Limited

Comparison
] ☐ A  Same as Previous
] ☐ B  No signific. change
] ☑C  Significant change

[ Open ]   [ ◁ ]

BP: ☐ / ☐
WT: ☐   BSA: ☐

FROM FIG. 8A stopFAX | C=6963 ROSENBLUM,LOUIS S311253 09/08/1997 TEE HR=1BP138/8
        | P=6831 ROSENBLUM,LOUIS S311253 09/02/1997 TTE HR=72BP94/69

FIG. 9A

CardioReportShell

VALVES

- ● Mitral
- ○ Tricuspid
- ○ Aortic
- ○ Pulmonic

☐ Normal ☐ NWV

Regurgitation

| O | A | B | C | D | E | F | G |

M <=== Morphology ===> T

- ☐ ☑ A  Normal  A ☐ ☐
- ☐ ☐ B  Mild SCC/NST  B ☐ ☐
- ☐ ☐ C  Mild MAC  C ☐ ☐
- ☐ ☐ D  Abnormal  D ☐ ☐
- ☐ ☐ E  Prosthesis  E ☐ ☐

M<=== Velocity ===>T

- ☐ ☑ A  Normal  A ☐ ☐
- ☐ ☐ B  Inc'd due to flow  B ☐ ☐
- ☐ ☐ C  Decreased  C ☐ ☐
- ☐ ☐ D  Stenotic  D ☐ ☐
- ☐ ☐ E  Not obtained  E ☐ ☐

1. Anatomy
- ☐ [A] Thickened
- ☐ ☐ B Myxomatous
- ☐ ☐ C Rheumatic
- ☐ ☐ D Mitral annular dilitation
- ☐ ☐ E Abscess
- ☐ ☐ F Nonspecific

2. Excursion
- ☐ [A] Decreased AML excursion
- ☐ [B] Decreased PML excursion
- ☐ ☐ C Doming
- ☐ ☐ D Immobile PML
- ☐ ☐ E Flail
- ☐ ☐ F Malcoaptation: chordal disrup
- ☐ ☐ G Malcoaption: popillary dysfun

3. Prolapse
- ☐ ☐ A Systolic bowing without prolaps
- ☐ [B] AML
- ☐ [C] PML
- ☐ ☐ D No MVP

4. SAM
- ☐ [A] Severity

TO FIG. 9B

| Exit | Generate | Edit | Sign | Print/View | Undo all |

FIG. 9B

OTHER

Pericardium/etc.
- ☐ ☐ A Normal
- ☐ ☐ B Minimal effusion
- ☐ ☑ C Abnormalities

Thrombus
- ☐ ☐ A None but LAA NWV
- ☐ ☐ B Inadequate to excl.
- ☐ ☐ C Thrombus

Miscellaneous
- ☐ ☐ A Congental
- ☐ ☑ B Contrast
- ☐ ☐ C No Vegetation
- ☐ ☐ D No Vegetation but CRO

Image quality
- ☐ ☐ A Technically difficult
- ☐ ☐ B Adequate
- ☐ ☑ C Good
- ☐ ☐ D Excellent
- ☐ ☐ E Limited

Comparison
- ☐ ☐ A Same as Previous
- ☐ ☐ B No signific. change
- ☐ ☑ C Significant change

[Open]  ◁

HR: ☐   BP: ☐ / ☐
HT: ☐   WT: ☐   BSA: ☐

FROM FIG. 9A

5. MAC
- ☐ ☑A Severity
- ☐ ☐B extension – PML
- ☐ ☐C extension – AML
- ☐ ☐D extension – SMA

6. Mass
- ☐ ☐A AML: ☐ mm
- ☐ ☐B PML: ☐ mm
- ☐ ☐C Atrial surface
- ☐ ☐D Ventricular surface

7. Vegetation
- ☐ ☐A Yes
- ☐ ☐B No
- ☐ ☐C Uncertain

8. Stenosis
- ☐ ☑A Severity
- ☐ ☐B Mean Gradient ☐ mm
- ☐ ☐C Undetermined

9. Valve area
- ☐ ☐A Planimetry: ☐ cm²
- ☐ ☐B P 1/2 ☐ cm²
- ☐ ☐C Continuity ☐ cm²
- ☐ ☐D PISA ☐ cm²

[Close]  ◁ stopFAX
C=6963 ROSENBLUM,LOUIS S311253 09/08/1997 TEE HR=IBP138/8
P=6831 ROSENBLUM,LOUIS S311253 09/02/1997 TTE HR=72BP94/69

FIG. 10A

CardioReportShell

VALVES

- ○ Mitral  ● Tricuspid
- ○ Aortic  ○ Pulmonic

☐ Normal  ☐ NWV

Regurgitation

| O | A | B | C | D | E | F | G |

M <=== Morphology ===> T

| | ☐ A | Normal | A ☐ ☐ |
| | ☐ B | Mild SCC/NST | B ☐ ☐ |
| | ☐ C | Mild MAC | C ☐ ☐ |
| | ☐ D | Abnormal | D ☐ ☐ |
| | ☐ E | Prosthesis | E ☐ ☐ |

M <=== Velocity ===> T

| | ☐ A | Normal | A ☐ ☐ |
| | ☐ B | Inc'd due to flow | B ☐ ☐ |
| | ☐ C | Decreased | C ☐ ☐ |
| | ☐ D | Stenotic | D ☐ ☐ |
| | ☐ E | Not obtained | E ☐ ☐ |

16. Anatomy
- ☐ ☐ A Thickened
- ☐ ☐ B Myxomatous
- ☐ ☐ C Rheumatic
- ☐ ☐ D Carcinoid
- ☐ ☐ E Annular dilitation
- ☐ ☐ F Abscess
- ☐ ☐ G Nonspecific

17. Excursion
- ☐ ☐ A Bowing
- ☐ ☐ B Prolapse
- ☐ ☐ C Decreased
- ☐ ☐ D Immobile
- ☐ ☐ E Flail
- ☐ ☐ F Malcoaptation

18. Mass
- ☐ ☐ A Anterior leaflet ☐ mm
- ☐ ☐ B Septal/posterior ☐ mm
- ☐ ☐ C Atrial surface
- ☐ ☐ D Ventricular surface

19. Vegetation
- ☐ ☐ A Yes
- ☐ ☐ B No
- ☐ ☐ C Uncertain

TO FIG. 10B

| Exit | Generate | Edit | Sign | Print/View | Undo all |

FIG. 10B

FROM FIG. 10A

☐ ☐A Severity
☐ ☐B Mean gradient ☐ mmHg
☐ ☐C Undetermined

OTHER

Pericardium/etc.
☐ ☐A Normal
☐ ☐B Minimal effusion
☐ ☑C Abnormalities

Thrombus
☐ ☐A None but LAA NWV
☐ ☐B Inadequate to excl.
☐ ☐C Thrombus

Miscellaneous
☐ ☐A Congenital
☐ ☑B Contrast
☐ ☐C No Vegetation
☐ ☐D No Vegetation but CRO Image quality
☐ ☐A Technically difficult
☐ ☐B Adequate
☐ ☑C Good
☐ ☐D Excellent
☐ ☐E Limited Comparison
☐ ☐A Same as Previous
☐ ☐B No signific. change
☐ ☑C Significant change

| Open | ◁ |

| Close | ◁ | HR: ☐ BP: ☐ / ☐ |
| | | HT: ☐ WT: ☐ BSA: ☐ | stopFAX  C=6963 ROSENBLUM,LOUIS S311253 09/08/1997 TEE HR=1BP138/8
        P=6831 ROSENBLUM,LOUIS S311253 09/02/1997 TTE HR=72BP94/69

FIG. 11A

CardioReportShell

VALVES

○ Mitral  ○ Tricuspid
◉ Aortic  ○ Pulmonic

☐ Normal  ☐ NWV

Regurgitation

| O | A | B | C | D | E | F | G |

M <=== Morphology ===> T
- ☐☐ A  Normal         A ☐☐
- ☐☐ B  Mild SCC/NST   B ☐☐
- ☐☐ C  Mild MAC       C ☐☐
- ☐☐ D  Abnormal       D ☐☐
- ☐☑ E  Prosthesis     E ☐☐

M<=== Velocity ===>T
- ☐☐ A  Normal           A ☐☐
- ☐☐ B  Inc'd due to flow B ☐☐
- ☐☐ C  Decreased        C ☐☐
- ☐☐ D  Stenotic         D ☐☐
- ☐☐ E  Not obtained     E ☐☐

10. Anatomy
- ☐ ☐ A  Trileaflet
- ☐ ☐ B  Bileaflet
- ☐ ☐ C  Cannot R/O bileaflet
- ☐ ☐D Increased thickness
- ☐ ☐ E  Sclerocalcific
- ☐ ☐ F  Rheumatic
- ☐ ☐ G  Abscess
- ☐ ☐ H  Nonspecific

11. Excursion
- ☐ ☐ A  LtN
- ☐ ☐B Decreased
- ☐ ☐ C  Doming
- ☐ ☐ D  Mid systolic closure
- ☐ ☐ E  Prolapse
- ☐ ☐ F  Flail

12. Mass
- ☐ ☐ A  RCC: ☐ mm
- ☐ ☐ B  LCC: ☐ mm
- ☐ ☐ C  NCC: ☐ mm
- ☐ ☐ D  Ventricular surface
- ☐ ☐ E  Aortic surface

TO FIG. 11B

[ Exit ] [ Generate ] [ Edit ] [ Sign ] [ Print/View ] [ Undo all ]

FIG. 11B

13. Vegetation
- ☐ ☐ A Yes
- ☐ ☐ B No
- ☐ ☐ C Uncertain

14. Dynamic Gradient
- ☐ ☐ A LVOT/Rest : [ ] mmHg
- ☐ ☐ B LVOT/Valsalvo [ ] mmHg
- ☐ ☐ C Mid-cavity [ ] m/sec

15. Stenosis
- ☐ ☐A Severity
- ☐ ☐ B Mean gradient  15 mmHg
- ☐ ☐ C Mean gradient [ ] mmHg
- ☐ ☐ D Continuity [ ] cm²

FROM FIG. 11A

OTHER

Pericardium/etc.
- ☐ ☐ A Normal
- ☐ ☐ B Minimal effusion
- ☐ ☑C Abnormalities

Thrombus
- ☐ ☐ A None but LAA NWV
- ☐ ☐ B Inadequate to excl.
- ☐ ☐ C Thrombus

Miscellaneous
- ☐ ☐ A Congental
- ☐ ☑B Contrast
- ☐ ☐ C No Vegetation
- ☐ ☐ D No Vegetation but CRO

Image quality
- ☐ ☐ A Technically difficult
- ☐ ☐ B Adequate
- ☐ ☑ C Good
- ☐ ☐ D Excellent
- ☐ ☐ E Limited

Comparison
- ☐ ☐ A Same as Previous
- ☐ ☐ B No signific. change
- ☐ ☑ C Significant change Open ◁

HR: [ ]  BP: [ ] / [ ]
HT: [ ]  WT: [ ]  BSA: [ ]

Close  ◁ stop FAX
C=6963 ROSENBLUM,LOUIS S311253 09/08/1997 TEE HR=1 BP138/8
P=6831 ROSENBLUM,LOUIS S311253 09/02/1997 TTE HR= 72 BP 94/69

FIG. 12A

CardioReportShell

VALVES

○ Mitral ○ Tricuspid
○ Aortic ● Pulmonic

☐ Normal ☑ NWV

Regurgitation
[ 0 ][ A ][ B ][ C ][ D ][ E ][ F ][ G ]

| M <=== Morphology ===>T | |
|---|---|
| ☐ ☐ A Normal | A ☐ ☐ |
| ☐ ☐ B Mild SCC/NST | B ☐ ☐ |
| ☐ ☐ C Mild MAC | C ☐ ☐ |
| ☐ ☐ D Abnormal | D ☐ ☐ |
| ☐ ☐ E Prosthesis | E ☐ ☐ |

| M<=== Velocity ===>T | |
|---|---|
| ☐ ☐ A Normal | A ☐ ☐ |
| ☐ ☐ B Inc'd due to flow | B ☐ ☐ |
| ☐ ☐ C Decreased | C ☐ ☐ |
| ☐ ☐ D Stenotic | D ☐ ☐ |
| ☐ ☐ E Not obtained | E ☐ ☐ |

22. Anatomy/Excursion
- ☐ ☐A Thickened
- ☐ ☐B Systolic doming
- ☐ ☐C Decreased excursion
- ☐ ☐D Carcinoid

23. Stenosis
- ☐ ☐A Severity
- ☐ ☐B Mean Gradient ☐ mmHg

24. Vegetation
- ☐ ☐A Yes
- ☐ ☐B No
- ☐ ☐C Uncertain

TO FIG. 12B

[ Exit ] [ Generate ] [ Edit ] [ Sign ] [ Print/View ] [ Undo all ]

FIG. 12B

| OTHER |
|---|
| Pericardium/etc. |
| ☐ ☐ A Normal |
| ☐ ☐ B Minimal effusion |
| ☐ ☑C Abnormalities |
| Thrombus |
| ☐ ☐ A None but LAA NWV |
| ☐ ☐ B Inadequate to excl. |
| ☐ ☐ C Thrombus |
| Miscellaneous |
| ☐ ☐ A Congenital |
| ☐ ☑B Contrast |
| ☐ ☐ C No Vegetation |
| ☐ ☐ D No Vegetation but CRO |
| Image quality |
| ☐ ☐ A Technically difficult |
| ☐ ☐ B Adequate |
| ☐ ☑ C Good |
| ☐ ☐ D Excellent |
| ☐ ☐ E Limited |
| Comparison |
| ☐ ☐ A Same as Previous |
| ☐ ☐ B No signific. change |
| ☐ ☑ C Significant change |

Open ◁

FROM FIG. 12A

Close ◁

HR: ☐  BP: ☐ / ☐
HT: ☐  WT: ☐  BSA: ☐ stopFAX
C=6963 ROSENBLUM,LOUIS S311253 09/08/1997 TEE HR=1BP138/8
P=6831 ROSENBLUM,LOUIS S311253 09/02/1997 TTE HR=72BP94/69

FIG. 13A window_Prosthesis

Prosthesis- Pulmonic

TYPE
- ☐ ☐ A homograft
- ☐ ☐ B xenograft
- ☐ ☐ C mechanical tilting
- ☐ ☐ D mechanical bileaflet
- ☐ ☐ E mechanical ball and cage
- ☐ ☐ F prosthetic valve ring
- ☐ ☐ G mechanical NOS
- ☐ ☐ H prosthetic NOS

SEWING_RING
- ☐ ☐ A normal
- ☐ ☐ B dehiscience
- ☐ ☐ C partial dehiscience
- ☐ ☐ D abcess
- ☐ ☐ E vegetation
- ☐ ☐ F thrombus
- ☐ ☐ G pannus

EXCURSION
- ☐ ☐ A normal
- ☐ ☐ B reduced
- ☐ ☐ C pot well visualized

THICKNESS
- ☐ ☐ A normal
- ☐ ☐ B mildly
- ☐ ☐ C mildly to moderately
- ☐ ☐ D moderately
- ☐ ☐ E moderately to markedly
- ☐ ☐ F markedly

[ Close ]

VEGETATION
- ☐ ☐ A vegetation
- ☐ ☐ B no vegetation
- ☐ ☐ C possible

VELOCITY
- ☐ ☐ A normal
- ☐ ☐ B mean gradient [ ] mmHg
- ☐ ☐ C orifice area [ ] $cm^2$
- ☐ ☐ D obstructive lax [ ]

STENOSIS
- ☐ ☐ A no stenosis
- ☐ ☐ B mild stenosis
- ☐ ☐ C significant stenosis

REGURGITATION
- ☐ ☐ A periprosthetic
- ☐ ☐ B transprosthetic
- ☐ ☐ C ? peri vs. valvular
- ☐ ☐ D not determined

TO FIG. 13B

The Rush Heart Institute

ECHOCARDIOGRPHY REPORT
Rush-Presbyterian-St. Luke's Medical Center
1653 W. Congress Parkway, Chicago, IL 60612
Phone:(312)942-4602 Fax:(312)942-5829

① RUSH

Patient Name

| MR#: 5306286 | AGE: 54 | SEX: M |
|---|---|---|
| DOB: 05/06/1943 | HEART RATE: | BP: 138/74 mmHg |
| HEIGHT: 70 IN | WEIGHT: 174 LB | BSA: 1.97 |
| TAPE#: TTE-97-194 | FOOTAGE: 00:05:00-00:14:58 | LOCATION: IN_LAB |
| ROOM: | TECH: | PREVIOUS ECHO: NO |

STUDY TYPE: Transthoracic echocardiogram.
IMAGE QUALITY: This was a technically good echocardiographic study.
INDICATION: Assess pulmonary pressure. F/U RV size, function.

PRIMARY FINDINGS: Left ventricular size was normal. Left ventricular systolic performance was normal. Estimated peak right ventricular and pulmonary artery systolic pressures were mildly to moderately increased, in the range of 40-50 mm Hg.

DETAILED FINDINGS

LEFT VENTRICLE
- Left ventricular size was normal. Left ventricular systolic performance was normal. There was no evidence for discrete regional wall motion abnormalities.
- Left ventricular wall thickness was normal.

AORTIC VALVE and AORTA
- The aortic valve morphology was normal. Transaortic flow velocities were normal. There was no Doppler evidence for aortic valvular regurgitation.

MITRAL VALVE and LEFT ATRIUM
- The mitral valve morphology was normal. Transmitral flow velocities were normal. There was no Doppler evidence for mitral valvular regurgitation.

FIG. 14A

RIGHT VENTRICLE
- Right ventricular size was mildly to moderately increased. Right ventricular systolic performance was mildly to moderately decreased. Right ventricular wall thickness was mildly increased.

TRICUSPID VALVE and RIGHT ATRIUM
- The tricuspid valve morphology was normal. Transtricuspid flow velocities were normal. There was Doppler evidence for mild tricuspid valvular regurgitation.
- The inferior vena cava was normal.

PUMONIC VALVE and PULMONARY ARTERY
- The pulmonic valve morphology was normal. Transpulmonary flow velocities were normal. There was Doppler evidence for trivial pulmonic valvular regurgitation.
- The pulmonary artery was moderately dilated.

RIGHT HEART PRESSURES
- Estimated peak right ventricular and pulmonary artery systolic pressures were mildly to moderately increased in the range of 40-50mmHg.

OTHER FINDINGS
- Pericardium: There was a minimal pericardial effusion without hemodynamic compromise.

MEASUREMENTS
    Left Ventricular End-Diastolic Dimension : 47mm
    Left Ventricular End-Systolic Dimension : 24mm
    Left Ventricular Septal Thickness: 9mm
    Left Ventricular Posterior Wall Thickness: 9mm
    Left Ventricular Fractional Shortening : 48%
    Tricuspid Regurgitation Velocity: 3.2m/s
    Aortic Root Dimension : 32mm
    Pulmonary Artery Dimension : 35mm

---

ICD-9 CODE
416.0 Primary pulmonary hypertension

---

REFERRING PHYSICIAN(S)

---

Read and signed by

FIG. 14B

USER INTERFACE FOR ECHOCARDIOGRAPHIC REPORT GENERATION

BACKGROUND OF THE INVENTION

This invention relates generally to computer-user interfaces for generating medical reports, and more particularly, to a computer-user interface for generating echocardiographic reports.

An echocardiogram is a diagnostic procedure which uses ultrasound to take moving pictures of the heart. The images appear in black and white or color and may be recorded on video tape and paper tape for later analysis and reporting by the physician. From these pictures, it is possible to measure the size of each of the four chambers of the heart, to study the appearance and motion of the heart and to conclude how forcefully the heart muscles contract to move the blood into each chamber of the heart and out to the lungs and the rest of the organs of the body.

Since a large amount of detailed information must be evaluated, many computerized medical report generation systems have been developed. Some of the report generation systems are generic to medical reports; some are specific to echocardiographic reports. All of the report generation systems are based on a traditional computer-user interface design using nested menus and check boxes. In the traditional user interface, the user is presented with a menu from which he selects an item. Once an item is selected, a window "pops up" displaying a limited number of boxes to select. Some windows contain "buttons" to select a secondary window, and so on. To complete an echocardiographic report, the physician must complete each selection, then close the window or go back to the menu and select another menu item. In the case of an echocardiographic report, the large volume of data entry and analysis involves considerable physician time switching back and forth between windows and menu screens.

Several aspects of echocardiography require the grading of abnormalities on a semi-quantitative scale from normal to markedly abnormal. Generic report systems, including those which have some specifics for echocardiograms, do not permit such semi-quantitative grading, other than by allowing the physician to type in the grading in a comments field. Also, since a generic report system can be used differently by different physicians, not all echocardiogram reports will necessarily be the same, either in format or content. There is a need in cardiology to have uniform echocardiograph reporting so that echocardiograms from one patient to another and multiple echocardiograms for the same patient can be easily compared.

An example of a report generator package is described in "A Report Generator Package for Routing Laboratory Tests in a Hospital Cardiology Department," by T. Cochrane and A. W. Dunlop, *Computer Methods and Programs in Biomedicine* 20 (1985) pp. 63–68. In this article, the user is prompted to input data on a series of VDU screen displays. The system automatically jumps between fields and then the user must select the next page. Each screen display contains a limited number of data items to input as well as notation indicating the correct "normal" range for the item. However, there is no provision for grading the results semi-quantitatively. And, for echocardiographic reports, the user must cycle through a large number of screens to cover all the chambers of the heart and systems.

It is an object of the invention to provide a computer-user interface that facilitates rapid and accurate input of echocardiographic information by echocardiogram readers. It is another object of the invention to provide a computer-user interface that enables grading results on a semi-quantitative basis. It is yet another object of the invention to provide a computer-user interface that enables rapid comparison of individual echocardiographic findings.

SUMMARY OF THE INVENTION

To achieve the foregoing and other objects, a computer-implemented user interface for generating an echocardiographic report according to the invention includes three elements which are unique for echocardiographic reporting.

The echocardiographic reporting system consists of nearly 600 data elements in total. Approximately half of these represent the most commonly used data elements and these are displayed in a plurality of data windows on a single main window. The left-right symmetry within the heart is used to optimize screen real estate for viewing and input of echocardiographic data. Maximizing the amount of information displayed on a single screen is achieved by displaying paired cardiac structures, such as the left ventricle and right ventricle, left atrium and right atrium, aorta and pulmonary artery, mitral and tricuspid valve, aortic and pulmonary valve, in common areas of the screen.

The user specifies whether data input will occur for the left or the right sided structure, and all of the buttons for data input are then activated for only the structure of interest. Results are displayed for both the left and right hand structures using a series of buttons to the left or the right of the data element of interest. Reuse of data descriptions between left and right heart structures cuts the amount of screen real estate necessary to display pertinent information nearly in half, and allows the most commonly used descriptions to be displayed on a single screen without the need for the additional windowing or opening of nested menus. Thus the user can input data easily without having to window through many different screens to uncover specific detailed information relevant to echocardiographic reporting.

A second unique element of the user interface is a custom control for input and display of semi-quantitative echocardiographic data. Several aspects of echocardiography require the grading of abnormalities on a semi-quantitative scale from normal to markedly abnormal with increments including mild to moderate degrees of abnormality. The interface preferably uses a series of buttons which represent each of the elements of the semi-quantitative scale: normal, upper normal or trivial, mildly abnormal, mildly to moderately abnormal, moderately abnormal, moderately to markedly abnormal and markedly abnormal. The reuse of the same semi-quantitative scale throughout the interface permits comments on chamber sizes or degree of regurgitation of various valves to be standardized, easily entered and reviewed by the echocardiographic reader. In addition, there is preferably a corresponding color scale for each of the semi-quantitative measures, where normal is designated by green, and shades of abnormality range from yellow to orange to red, based on severity. This allows the viewer to easily discern from the interface, those parts of the echocardiograph which are most abnormal.

The third unique feature of the interface is the ability to compare previous echocardiographic reports for the same patient with the current report. Preferably, every echocardiographic report finding has two rows of buttons, the innermost button being the result of the current study and the outer buttons representing findings from previous studies. The inner and outer button displays may also occur on a semi-quantitative scale, allowing rapid visual comparison of findings from current and previous studies. This is extremely useful for echocardiographic readers and clinicians reviewing studies to quickly see where discrepancies and changes in cardiac function have occurred from one report to the next.

BRIEF DESCRIPTION OF THE DRAWINGS

FIG. 1 is a menu of patient echocardiographic reports on a system.

FIG. 2 is a first level screen showing the four sections of the echocardiogram.

FIG. 3 is a second level screen for a left ventricle.

FIGS. 5 and 6 are second level screens for a left and a right atrium, respectively, superimposed over a first level screen.

FIGS. 7 and 8 are second level screens for the aortic and pulmonary arteries, respectively, superimposed over a first level screen.

FIGS. 9, 10, 11 and 12 are second level screens for the mitral, tricuspid, aortic and pulmonic valves, respectively, superimposed over a first level screen.

FIG. 14 is an exemplary report generated from the report generation system after user input.

DETAILED DESCRIPTION OF THE INVENTION

Figure 4B:
FIG. 4 is a second level screen for a right ventricle.

In the computer-implemented user interface of the invention, FIG. 1 is a patient menu screen, the first screen seen by the user. The patient menu screen includes a list of patients for whom an echocardiographic report has been generated. By selecting the button to the left of the patient's name, then clicking on an action button at the bottom of the screen, the user can access the report to modify it or add new information and comments. Available actions include, reading, amending, search, view, new modify, TSE-DSE modify, send fax and check fax. If the number of patients exceeds the space available on the screen, a page down button can be selected to scroll through the rest of the patient listings.

Next to the patient's name are additional information including the date of the report, type of study, whether the echocardiogram has been read or not, type of data tape, length of the data tape, location of the tape and name of the technician administering the echocardiogram. To enter a new patient's echocardiogram report, the user selects "New" under "Action," then enters the patient's name and other information in the appropriate columns.

Once the user selects an existing patient report or adds a new patient, the first screen to appear is shown in FIG. 2. The screen in FIG. 2 is broken down into data entry windows, including four representing the four main divisions of the heart. Ventricles, Atria, Arteries and Valves are the main categories from which the user selects from one of two paired structures in each. In Ventricles, the user can select left ventricle, LV, or right ventricle, RV. In Atria, the user can select left atrium, LA, or right atrium, RA. In Arteries, the user can select aortic artery, AO, or pulmonary artery, PA. In Valves, the user can select Mitral, Aortic, Tricuspid or Pulmonic. Thus, heart symmetry is used to save screen real estate.

Additional data entry windows include heart rate and blood pressure, PA pressure, inferior vena cava (IVC), and central venous pressure (CVP). Under the window marked "Other," the user can complete information relating to the Pericardium, Thrombus, Miscellaneous (congenital, contrast, no vegetation, no vegetation but "cannot rule out", CRO), Image Quality and Comparison. At the bottom of the screen are action buttons to Exit, Generate Report, Edit, Sign, Print/View, Undo all, and Exit.

Several of the data entry windows include a custom control bar for input and display of semi-quantitative echocardiographic data. The interface uses a series of buttons designated by the letters A–G, which represent each of the elements of the semi-quantitative scale. A represents normal, B represents upper normal or trivial, C represents mildly abnormal, D represents mild-to-moderately abnormal, E represents moderately abnormal, F represents moderate-to-markedly abnormal, G represents markedly abnormal. The button to the left of A (0, + or −) represents either not obtained, greater than normal or smaller than normal. The reuse of the same semi-quantitative scale throughout the interface allows comments on chamber sizes or degree of regurgitation of various valves to be standardized and easily entered and reviewed by the echocardiographic reader. In addition, there is a corresponding color scale for each of the semi-quantitative measures, where normal is designated as green and shades of abnormality range from yellow to orange to red based on severity. This allows the viewer to easily discern from the interface parts of the echo that are most abnormal.

Additionally, each custom control contains two rows of buttons spaced in parallel to one another. The top row of buttons includes the patient's readings from the most recent previous echocardiogram (assuming the report is in the system). The bottom row contains the patient's readings from the current echocardiogram. In this way, the viewer can easily compare the patient's progress from the previous echocardiogram to the current.

FIG. 3 shows the secondary data entry screen (or window) which is displayed when the user selects the LV, or left ventricle, data entry window to complete. Note that this screen/window is smaller than the first data entry screen and is displayed on top of the first data entry screen. Data entry parameters for the left ventricle include size, thickness, function, wall motion, diastolic parameters, mass, hypertrophy, interventricular septum. Diastolic parameters include E/A ratio, deceleration time, pulmonary vein flow, IVRT and diastolic function. Selecting the close button closes the window and returns the user to the screen shown in FIG. 2.

FIG. 4 shows the secondary data entry screen which is displayed when the user selects the RV, or right ventricle, data entry window to complete. Note that this screen/window is smaller than the first data entry screen and is displayed on top of the first data entry screen. Data entry parameters for the right ventricle include size, thickness, function, wall motion, diastolic function and mass. Selecting the close button closes the window and returns the user to the screen shown in FIG. 2.

FIG. 5 shows the secondary data entry screen which is displayed when the user selects the LA, or left atrium, data entry window to complete. Note that this screen/window is smaller than the ventricle secondary screen and is displayed on top of the first data entry screen. Data entry parameters for the left atrium include size, LAA, septum and mass. Selecting the close button closes the window and returns the user to the screen shown in FIG. 2.

Figure 6B:
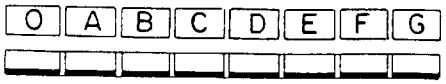

FIG. 6 shows the secondary data entry screen which is displayed when the user selects the RA, or right atrium, data entry window to complete. Note that this screen/window is smaller than the ventricle secondary screen and is displayed on top of the first data entry screen. Data entry parameters for the right atrium include size, RAA, septum and mass. Selecting the close button closes the window and returns the user to the screen shown in FIG. 2.

Figure 7B:
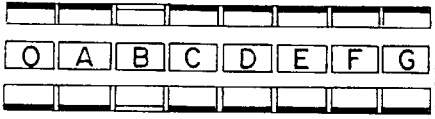

FIG. 7 shows the secondary data entry screen which is displayed when the user selects the AO, or aorta, data entry window to complete. Note that this screen/window is smaller than the ventricle secondary screen and is displayed on top of the first data entry screen. Data entry parameters for the aortic artery include size, dissection and aortic arch. Selecting the close button closes the window and returns the user to the screen shown in FIG. 2.

FIG. 8 shows the secondary data entry screen which is displayed when the user selects the PA, or pulmonary artery, data entry window to complete. Note that this screen/window is smaller than the ventricle secondary screen and is displayed on top of the first data entry screen. Data entry parameters for the pulmonary artery include size. Selecting the close button closes the window and returns the user to the screen shown in FIG. 2.

FIG. 9 shows the secondary data entry screen which is displayed when the user selects the mitral valve data entry window to complete. Note that this screen/window is smaller than the ventricle secondary screen and is displayed on top of the first data entry screen. Data entry parameters for the mitral valve include regurgitation, morphology, velocity, anatomy, excursion, prolapse, SAM, MAC, mass, vegetation, stenosis and valve area. Selecting the close button closes the window and returns the user to the screen shown in FIG. 2.

FIG. 10 shows the secondary data entry screen which is displayed when the user selects the tricuspid valve data entry window to complete. Note that this screen/window is smaller than the ventricle secondary screen and is displayed on top of the first data entry screen. Data entry parameters for the tricuspid valve include regurgitation, morphology, velocity, anatomy, excursion, mass, vegetation and stenosis. Selecting the close button closes the window and returns the user to the screen shown in FIG. 2.

FIG. 11 shows the secondary data entry screen which is displayed when the user selects the aortic valve data entry window to complete. Note that this screen/window is smaller than the ventricle secondary screen and is displayed on top of the first data entry screen. Data entry parameters for the aortic valve include regurgitation, morphology, velocity, anatomy, excursion, mass, vegetation, dynamic gradient and stenosis. Selecting the close button closes the window and returns the user to the screen shown in FIG. 2.

FIG. 12 shows the secondary data entry screen which is displayed when the user selects the pulmonic valve data entry window to complete. Note that this screen/window is smaller than the ventricle secondary screen and is displayed on top of the first data entry screen. Data entry parameters for the pulmonic valve include regurgitation, morphology, velocity, anatomy, excursion, mass, vegetation, dynamic gradient and stenosis. Selecting the close button closes the window and returns the user to the screen shown in FIG. 2.

Figure 13B:
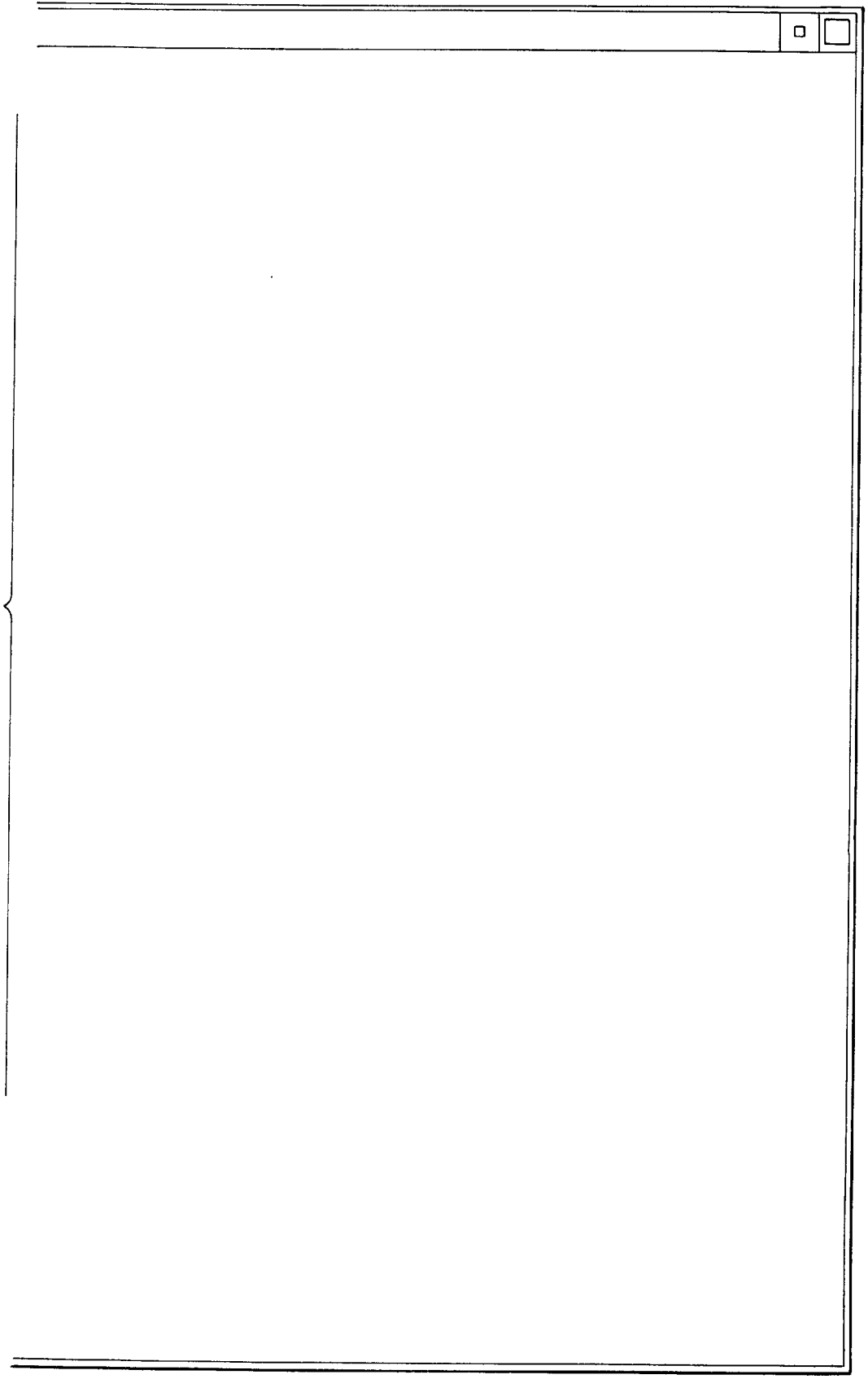
FIG. 13 is a second level screen for a valve prothesis.

FIG. 13 shows a secondary data entry screen for an example of a valve prosthesis for the pulmonic position, which is displayed when the user selects the prosthesis data entry window to complete. Note that this screen/window is smaller than the ventricle secondary screen and is displayed on top of the first data entry screen. Data entry parameters for the valve prosthesis include type, sewing ring, excursion, thickness, vegetation, velocity, stenosis and regurgitation.

FIG. 14 is a sample report which is generated by the user interface when the user selects "Generate" on the action button on the first data entry screen. The report includes patient information, and detailed findings for all of the heart categories described above: left ventricle, right ventricle, aortic valve and aorta, mitral valve and left atrium, tricuspid valve and right atrium, pulmonic valve and pulmonic artery, right heart pressures, other findings and measurements. Once the report is generated, it can be faxed to recipients or generated in html and distributed on the user's network.

Referring again to FIG. 2, the action button "Sign" permits the user physician who prepares the report or approves the report to sign off on the report on-line.

While there have been illustrated and described particular embodiments of the invention, it will be appreciated that numerous changes and modifications will occur to those skilled in the art, and it is intended in the appended claims to cover all those changes and modifications which fall within the true spirit and scope of the invention.

What is claimed is:

1. A computer-implemented user interface for generating an echocardiographic report, comprising:

a patient menu screen, wherein said patient menu screen includes means for selecting an existing patient record and means for establishing a new patient record;

means for displaying a first echocardiographic data screen responsive to a first user input for selecting a desired one of said existing patient records and for establishing said new patient record, wherein said first screen includes a plurality of data entry windows for entering echocardiographic data, wherein at least one data entry window displays echocardiographic data for two paired cardiac structures;

means for selecting a desired one of said paired cardiac structures; and means for entering patient data pertaining to a selected cardiac structure.

2. The interface of claim 1 wherein said paired cardiac structures comprise left ventricle and right ventricle, left atrium and right atrium, aorta and pulmonary artery, mitral and tricuspid valve, and aortic and pulmonary valve.

3. The interface of claim 1 wherein each data entry window includes means for selecting a second data entry window pertaining to a cardiac structure and further comprising:

means for displaying a second echocardiographic data screen responsive to a second user input for selecting a second data entry window, wherein said second data entry window includes means for entering patient data pertaining to said cardiac structure.

4. The interface of claim 3 wherein said paired cardiac structures comprise left ventricle and right ventricle, left atrium and right atrium, aorta and pulmonary artery, mitral and tricuspid valve, and aortic and pulmonary valve.

5. The interface of claim 1 wherein each data entry window includes means for displaying semi-quantitative echocardiographic data pertaining to a cardiac structure.

6. The interface of claim 5 wherein said semi-quantitative means comprises a plurality of buttons wherein each button represents an element of the semi-quantitative scale.

7. The interface of claim 6 wherein the semi-quantitative scale includes normal, upper normal, mildly abnormal, mildly to moderately abnormal, moderately abnormal, moderately to markedly abnormal.

8. The interface of claim 7 wherein said semi-quantitative scale further includes a corresponding color scale.

9. The interface of claim 1 further comprising means for displaying a patient's previous echocardiographic report data comprising first and second rows of buttons wherein the first row displays data from the patient's previous report and the second row displays data from the patient's current report.

10. The interface of claim 1 further comprising means for generating an echocardiographic report.

11. A computer-implemented method for providing a user interface for echocardiographic report generation, the method comprising the steps of:

displaying a patient menu screen wherein said patient menu screen includes means for selecting an existing patient record and means for establishing a new patient record;

displaying a first echocardiographic data screen in response to a first user input for selecting a desired one of said existing patient records and for establishing said new patient record wherein said first screen includes a plurality of data entry windows for entering echocardiographic data, wherein at least one data entry window displays echocardiographic data for two paired cardiac structures;

selecting a desired one of said paired cardiac structures; and entering patient data pertaining to a selected cardiac structure.

12. The method of claim 11 wherein said paired cardiac structures comprise left ventricle and right ventricle, left atrium and right atrium, aorta and pulmonary artery, mitral and tricuspid valve, and aortic and pulmonary valve.

13. The method of claim 11 wherein each data entry window includes means for selecting a second data entry window pertaining to a cardiac structure and further comprising the step of:

displaying a second echocardiographic data screen in response to a second user input for selecting a second data entry window, wherein said second data entry window includes means for entering patient data pertaining to said cardiac structure.

14. The method of claim 13 wherein said paired cardiac structures comprise left ventricle and right ventricle, left atrium and right atrium, aorta and pulmonary artery, mitral and tricuspid valve, and aortic and pulmonary valve.

15. The method of claim 11 wherein each data entry window includes means for displaying semi-quantitative echocardiographic data pertaining to a cardiac structure.

16. The method of claim 15 wherein said semi-quantitative means comprises a plurality of buttons wherein each button represents an element of the semi-quantitative scale.

17. The method of claim 16 wherein the semi-quantitative scale includes normal, upper normal, mildly abnormal, mildly to moderately abnormal, moderately abnormal, moderately to markedly abnormal.

18. The method of claim 17 wherein said semi-quantitative scale further includes a corresponding color scale.

19. The method of claim 11 further comprising the step of displaying a patient's previous echocardiographic report data in a first row of buttons and displaying a patient's current echocardiographic report data in a second row of buttons.

20. The method of claim 11 further comprising the step of generating an echocardiographic report.

* * * * *